United States Patent [19]

Atkinson et al.

[11] Patent Number: 4,863,928

[45] Date of Patent: Sep. 5, 1989

[54] METHOD OF TREATMENT FOR ARTHRITIC AND INFLAMMATORY DISEASES

[75] Inventors: David C. Atkinson, Pembroke Pines; Jack Fishman, Miami; Fred P. Sherman, Hollywood, all of Fla.

[73] Assignee: Baker Cummins Pharmaceuticals, Inc., Miami, Fla.

[21] Appl. No.: 293,196

[22] Filed: Jan. 4, 1989

[51] Int. Cl.$^4$ .................................................. A61K 31/44
[52] U.S. Cl. ...................................................... 514/282
[58] Field of Search ........................................ 514/282

[56] References Cited

U.S. PATENT DOCUMENTS 4,760,069 7/1988 Rzeszotarski et al. .............. 574/282

OTHER PUBLICATIONS

Chem. Abst. 107 (1987)-229062x.
Rios et al., *Eur. J. Pharm.*, 96:277-283 (1983).
Kayser et al., *Proceedings of the Vth World Congress on Pain*, pp. 72-79 (Elsevier Science Publishers 1988).
Hargreaves et al., *Proceedings of the Vth World Congress on Pain*, pp. 55-60 (Elsevier Science Publishers 1988).

*Primary Examiner*—Stanley J. Friedman
*Attorney, Agent, or Firm*—Kirschstein, Ottinger, Israel & Schiffmiller

[57] ABSTRACT

A method of treating a human or animal patient suffering from an arthritic disease or associated inflammatory disease comprises daily administration to such patient of from about 1 to about 100 mg of the narcotic antagonists nalmefene or naltrexone. The nalmefene or naltrexone may be administered in equally divided doses from one to four times daily, preferably by the oral route. Parental administration may be utilized where suitable.

10 Claims, No Drawings

METHOD OF TREATMENT FOR ARTHRITIC AND INFLAMMATORY DISEASES

BACKGROUND OF THE INVENTION

1. Field of the Invention

The invention relates to methods of treating arthritic diseases and associated inflammatory diseases.

2. Description of the Prior Art

Arthritic diseases are characterized by joint inflammation, although the etiology of the inflammation may differ in various conditions. Relatively common arthritic diseases include rheumatoid arthritis, juvenile arthritis, ankylosing spondylitis, psoriatic arthritis and osteoarthritis, often referred to as degenerative joint disease.

Most forms of arthritis are treated initially with nonsteroidal anti-inflammatory drugs, sometimes together with other analgesics. Where the disease is not adequately controlled with these agents, disease-modifying (remission-inducing) antirheumatic drugs, such as gold salts, D-penicillamine, antimalarial agents and cytotoxic agents, may be utilized. Ultimately, glucocorticoids may be administered, systemically or by the intra-articular route. None of these drugs is significantly effective in achieving true remission of the disease in most patients.

Moreover, all of the currently practiced drug treatments for arthritic diseases have significant drawbacks. Apart from gastrointestinal disturbances, the nonsteroidal anti-inflammatory drugs may cause renal dysfunction in susceptible individuals. The antimalarials may cause serious retinopathy which can occur several years after initiation of therapy. Chronic glucocorticoid therapy is associated with a number of pernicious side effects, including hypertension, adrenal suppression, excessive immunosuppression and CNS dysfunction. Immunosuppressive and cytotoxic agents can cause bone marrow depression and lead to serious infection.

The inflammatory process is mediated by a variety of endogenous substances which can be categorized as follows: vasoactive substances, chemotactic factors, and agents causing cell and tissue damage. Among the vasoactive substances are histamine, serotonin, protein constituents of the complement system, bradykinin, and prostaglandins. Prostaglandin levels are increased in the synovial fluid of patients with rheumatoid arthritis and osteoarthritis. All effective nonsteroidal anti-inflammatory drugs inhibit prostaglandin systhesis, thereby reducing the concentration of prostaglandins. See generally *American Medical Association Drug Evaluations* (6th ed., 1986), p. 1049.

Tissue damage in inflammatory diseases results from the complex interplay of humoral and cellular immune responses. In rheumatoid inflammation, antigen-antibody complexes accumulate in synovial tissues and activate the complement system, leading to the release of inflammatory mediators, including lysosomal enzymes, prostaglandins, and free oxygen radicals. It has been hypothesized that many of the manifestations of joint damage occurring in arthritis could be the result of damaging free oxygen radicals, large amounts of which are released together with powerful digestive enzymes into the arthritic joint by polymorphonuclear leukocytes undergoing "frustrated phagocytosis." These radicals have been shown to degrade DNA and hyaluronic acid, a major constituent of synovial fluid, and, to some extent, to degrade also collagen and elastin. Moreover, oxidants can activate latent collagenase, possibly by inactivating protease inhibitors, leading ultimately to cartilage destruction.

It is known that inflammatory cells such as polymorphonuclear leukocytes have opiate receptors. The endogenous opioid B-endorphin has been shown in vitro to stimulate superoxide radical production by human polymorphonuclear leukocytes via an opiate receptor. This superoxide production has been shown to be abolished by equimolar concentrations of the opiate antagonist naloxone. B. M. Sharp et al., *J. Pharm. Exp. Ther.*, 242(2):579–582 (1987). Naloxone has also been shown to inhibit in vitro the production of superoxide from human neutrophils stimulated with N-formyl-methionyl-leucyl-phenylalanine, which effect is not opiate receptor-mediated, nor is it the result of superoxide scavenging. Simpkins et al., *Life Sciences*, 37:1381–1386 (1985).

Systemically-administered naloxone has been shown to exert tissue-protective effects in a variety of experimental and clinical conditions in which the damaging effects of superoxide radicals and their derived oxygen species (hydrogen peroxide and the hydroxyl radical) are believed to play a major role. In particular, naloxone has been recently shown to have a protective effect on the ultrastructure of the ischemic canine kidney. H. K. Elkadi et al., *J. Surg. Res.*, 42:675–692 (1987).

Despite the foregoing, neither naloxone nor any other opioid antagonist has been disclosed heretofore as clinically useful in the treatment of the inflammatory manifestations of arthritic diseases. There has also been no suggestion that such antagonists might not only relieve inflammation but also cause true remission in such diseases.

SUMMARY OF THE INVENTION

It is the object of the present invention to provide a method of treatment for arthritic diseases and related inflammatory conditions which avoids the drawbacks and disadvantages of the prior art drug treatment methods while achieving dramatic symptomatic relief. In keeping with this object and others that will become apparent hereinafter, the present invention resides in the daily administration to patients suffering from arthritic diseases or associated inflammatory conditions of from about 1 to about 100 milligrams of either of the narcotic antagonists nalmefene or naltrexone. The oral route of administration is preferred for patient convenience, comfort and safety.

DETAILED DESCRIPTION OF THE INVENTION

Nalmefene (6-methylene-6-desoxy-N-cyclopropylmethyl-14-hydroxydihydronormorphine) is a long-acting, orally available, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia (U.S. Pat. No. 4,511,570) and sudden infant death syndrome (U.S. Pat. No. 4,639,455), among others. Nalmefene has not hitherto been disclosed, however, as having any utility in the treatment of arthritic or inflammatory diseases.

Naltrexone (N-cyclopropylmethyl-14-hydroxydihydromorphinone) is another orally available narcotic antagonist with pure antagonist activity. Naltrexone has additionally been disclosed as useful for inducing anorexia (U.S. Pat. Nos. 4,477,457; 4,478,840) and for treating shock (U.S. Pat Nos. 4,267,182; 4,434,168) but not for the treatment of arthritic or inflammatory diseases.

The method of the present invention consists of the daily administration to human or animal patients suffering from an arthritic disease of from about 1 to about 100 mg of nalmefene or naltrexone. The oral route of administration is preferred so that the patient can self-medicate safely and conveniently. Nalmefene and naltrexone, unlike certain other narcotic antagonists (e.g. naloxone), are highly effective and substantially bioavailable when administered orally. Nalmefene and naltrexone can be administered parenterally as well, however, for purposes of the present invention.

As used herein, the term "arthritic disease" refers to any disease state characterized by significant joint inflammation. Among such arthritic diseases are rheumatoid arthritis, juvenile rheumatoid arthritis, ankylosing spondylitis, osteoarthritis, Reiter's syndrome, psoriatic arthritis and acute gouty arthritis. The treatment of inflammatory conditions which often occur in conjunction with arthritis, such as bursitis and tendinitis, is also comprehended by the present invention.

In accordance with the present invention, nalmefene or naltrexone may be administered to patients suffering from an arthritic disease or an associated inflammatory disease (e.g., bursitis or tendinitis) in any conventional oral or parenteral dosage form. Oral dosage forms may include tablets, capsules, caplets, liquids, and the like, including generally from about 0.5 to about 50.0 mg of nalmefene or naltrexone per dosage unit together with suitable pharmaceutically-acceptable excipients, binders, sweeteners, coloring agents and other conventional additives. Parenteral dosage forms may include any conventional injectable solutions of nalmefene or naltrexone, for example an isotonic saline solution together with pharmaceutically-acceptable preservatives and buffers. The parenteral dosage forms generally contain from about 0.5 to about 50.0 mg of nalmefene or naltrexone and may be injected by the subcutaneous, intramuscular, intravenous or intra-articular routes.

By one preferred method, the nalmefene or naltrexone may be initially administered to patients in two daily doses of 1 or 2 mg each, for example for a one-week period, with gradual increments of 1 or 2 mg b.i.d. up to a maximum of 50 mg b.i.d.

The method of the present invention provides effective symptomatic relief for patients suffering from arthritic diseases or associated inflammatory conditions. It is believed that in many instances, true remission of arthritic and inflammatory diseases can be achieved.

Apart from systemic routes of administration, nalmefene or naltrexone may be administered to arthritis patients locally at a disease site—for example, injected intra-articularly in the case of rheumatoid arthritis or osteoarthritis patients. Nalmefene is particularly well-suited for both systemic and local use because of its long duration of action.

Although there may be no need to administer the nalmefene or naltrexone more than once or twice daily to achieve the results envisioned by the present invention, equally divided doses administered up to four times daily may be utilized. There have been few reports of any significant adverse effects with nalmefene or naltrexone therapy at the dosage levels proposed by the present invention, unlike many of the pharmaceutical agents which have been conventionally used to treat arthritic and inflammatory diseases.

The following example provides a detailed illustration of the method of the present invention. This example is not intended to limit or restrict the scope of the invention in any way, and should not be construed as providing dosage forms, regimens or methods of administration which must be utilized exclusively to practice the invention.

EXAMPLE

A patient exhibiting symptoms of small joint arthritis, among other symptoms, was administered a 1.0 mg tablet of nalmefene twice daily for seven days after which the dosage was increased in weekly increments of 1 mg b.i.d. until she was receiving 10 mg b.i.d. When the patient reached a dosage level of 6 mg of nalmefene b.i.d., she noted a marked reduction in her joint pain associated with a lessening in her sensation of fatigue.

The patient has been maintained at a dosage level of 10 mg of nalmefene b.i.d. for about four months. She no longer requires concomitant medications for her arthritis and is able to perform manual activities without pain. Her blood count, electrolytes, renal function, liver enzymes and clotting parameters continue to be in the normal range.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A method of treating a human or animal patient suffering from an arthritic disease or associated inflammatory disease comprising the daily administration to the patient of from about 1 to about 100 mg of nalmefene or naltrexone.

2. A method according to claim 1 wherein said patient is suffering from an arthritic disease selected from the group consisting of rheumatoid arthritis, juvenile rheumatoid arthritis, osteoarthritis, ankylosing spondylitis, psoriatic arthritis, acute gouty arthritis and Reiter's syndrome.

3. A method according to claim 1 wherein said patient is suffering from an inflammatory disease selected from the group consisting of bursitis and tendinitis.

4. A method according to claim 1 wherein the nalmefene or naltrexone is administered to the patient orally.

5. A method according to claim 4 wherein the nalmefene or naltrexone is administered to the patient in an oral dosage form comprising a tablet, capsule, caplet or liquid containing from about 0.5 to about 50.0 mg of nalmefene or naltrexone per unit.

6. A method according to claim 1 wherein the nalmefene or naltrexone is administered to the patient parenterally.

7. A method according to claim 6 wherein the nalmefene or naltrexone is administered to the patient by the subcutaneous, intramuscular, intravenous or intra-articular routes.

8. A method according to claim 1 wherein the nalmefene or naltrexone is administered to the patient from one to four times daily.

9. A method according to claim 8 wherein the nalmefene or naltrexone is administered to the patient from one to two times daily.

10. A method according to claim 9 wherein 1 mg of nalmefene or naltrexone is administered to the patient twice daily for an initial period, after which the dosage amount is gradually increased to a maximum of 50 mg twice daily.

* * * * *